United States Patent [19]

Goodhue et al.

[11] Patent Number: 5,418,151
[45] Date of Patent: May 23, 1995

[54] REGIO-SELECTIVE PROCESS FOR RESOLUTION OF CARBOHYDRATE MONOESTERS

[75] Inventors: Charles T. Goodhue; Theresa C. Paulson; Robert Seemayer, all of Rochester, N.Y.

[73] Assignee: Genencor International, Inc., Rochester, N.Y.

[21] Appl. No.: 926,874

[22] Filed: Aug. 7, 1992

[51] Int. Cl.⁶ .......................... C12P 19/02; C12P 7/64; C12P 7/40

[52] U.S. Cl. .................................. 435/105; 435/134; 435/136; 435/197; 435/280; 435/921; 435/931; 435/933

[58] Field of Search ............... 435/280, 105, 134, 136, 435/197, 921, 931, 933

[56] References Cited

U.S. PATENT DOCUMENTS 4,327,183  4/1982  Masuda et al. .
4,614,718  9/1986  Seino et al. .

FOREIGN PATENT DOCUMENTS

0413307A1  2/1991  European Pat. Off. .

OTHER PUBLICATIONS

APS Abstract of Japan 02-6059 (Mar. 1, 1990) Ota et al. Published ABS Date May 18, 1990.
APS Abstract of Japan 56-151496 (Nov. 24, 1981) Masuda et al. Published Date ABS Mar. 3, 1982.
Chemical Abstracts, vol. 116, No. 9, Mar. 1992, p. 692 CA:82246k Miyake et al.

*Primary Examiner*—Herbert J. Lilling
*Attorney, Agent, or Firm*—Margaret A. Horn

[57] ABSTRACT

There is provided a regio-selective method for the resolution of carbohydrate monoester mixtures, by treating such mixtures with one or more selective enzymes. The resolution of such mixtures results in monoesters comprising significantly purer isolates of one desired isomer.

13 Claims, No Drawings

REGIO-SELECTIVE PROCESS FOR RESOLUTION OF CARBOHYDRATE MONOESTERS

FILED OF THE INVENTION

This invention relates to the biosynthetic preparation of carbohydrate monoesters, which preparation is selective for the preparation of one or more positional isomers of such monoester. More particularly, this invention relates to the preparation of sucrose monoesters by selective hydrolysis of specific components of mixtures of sucrose monoesters by contacting such mixtures with specific enzymes. In addition, this invention relates to the use of monoesters made by the process of the present invention as excipients in pharmaceuticals, foods, cosmetics or as emulsifiers, coating agents, antiseptic agents and the like.

BACKGROUND OF THE INVENTION

Carbohydrate monoesters, and specifically sucrose monoesters, are used commercially as food emulsifying agents, as coating agents and as excipients in pharmaceutical, cosmetic and other products. Commercially available monoesters, typically made by chemical means, comprise mixtures of positional isomers or are often mixed with an amount of di- and tri-esters (usually at about 20% of the mixture). However, there is no commercially feasible synthesis that selectively yields pure monoesters, that is monoesters which substantially comprise one positional isomer of a monoester such as the 6-O, 6'-O or 1'-O monoester. If commercially available mixtures made by chemical means could be resolved such that specific isomers of the monoesters could be isolated, it would be advantageous since by selective isolation of the isomers the monoesters may have unique properties for food and cosmetic uses compared to the mixtures.

Therefore, there is a need for a process for the resolution of regio-selective isomers of carbohydrate monoesters, and particularly sucrose monoester. It is an object of this invention to provide a method to resolve a mixture of carbohydrate monoesters obtained by chemical reaction into monoesters of defined structure which comprise substantially the 6-O-ester, the 1'-O-ester or the 6'-O-ester.

SUMMARY OF THE INVENTION

This invention relates to a regio-selective method for the resolution of a mixture of carbohydrate monoesters, the method comprising incubating the ester mixture in an appropriate solvent system with one or more regio-selective enzymes and purifying the desired monoester.

In an embodiment of this invention, the carbohydrate monoester (or mixture thereof) is a sucrose or glucose monoester of a fatty acid of at least about 8 carbon atoms in length, and preferably about 8–22 carbon atoms. Most preferred are monoesters of a fatty acid of about 8–18 carbon atoms. Specifically preferred embodiments of the present invention comprise a carbohydrate which is glucose or sucrose and a fatty acid which is palmitate, laurate or caprate. The structure of sucrose monopalmitate and glucose-6-palmitate are provided below in order to show an illustration of what is meant by the 6-O, 1'-O and 6'-O esters, as well as to show varying fatty acid chain lengths. These structures should not be viewed as limiting the present invention.

GLUCOSE-6-PALMITATE

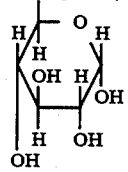

SUCROSE MONOPALMITATE

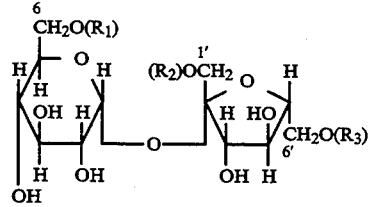

| | |
|---|---|
| 6-O-ester | $R_1$ = palmitate<br>$R_2$ = H<br>$R_3$ = H |
| 6'-O-ester | $R_1$ = H<br>$R_2$ = H<br>$R_3$ = Palmitate |
| 1'-O-ester | $R_1$ = H<br>$R_2$ = Palmitate<br>$R_3$ = H |

Enzymes useful in the present invention are those enzymes which selectively hydrolyze certain components of the monoesters, and particularly those enzymes which hydrolyze primary alcohols on the carbohydrate. Useful enzymes include but are not limited to esterases, lipases, proteases or glycosidases or mixtures thereof.

DETAILED DESCRIPTION OF THE INVENTION

Presently, esters made by chemical, acid or base-catalyzed reactions of sucrose with fatty acid acyl donors are about 90% esters resulting from esterification of the three primary alcohol groups of sucrose. The remaining 10% is made up of esters of secondary alcohol groups on the sucrose. Such commercially available esters typically comprise a mixture of the 6-O-ester, the 1'-O-ester and the 6'-O-ester. Typically the 6-O and 6'-O esters are present in approximately equal amounts and the 1'-O-ester is about 20% of the combined amount of the 6-O and 6'-O-esters. The remaining amount of monoesters consist of compounds with the five secondary alcohols in the sucrose molecule. The proportion of monoesters found in the eight alcohol functions on sucrose is in direct relationship to the chemical reactivity at those positions.

It has been found that by using regio-selective enzymes, it is possible to resolve a mixture of carbohydrate monoesters obtained by chemical reaction into monoesters of defined structure which defined structures are comprised substantially of one of the following esters: 6-O, 1'-O or 6'-O esters. The process of the present invention comprises incubating a mixture of carbohydrate monoesters in an appropriate solvent system with specific

TABLE 1

| Enzyme Identification | Source | Supplier | Ester Specificity |
|---|---|---|---|
| Amyloglucosidase | Rhizopus sp. | Sigma | 6'- |
| Amyloglucosidase | *Aspergillus niger* | Sigma | 6'-, 1'- |
| AP-6 | *Aspergillus niger* | Amano | A |
| *Aspergillus niger* lipase | *Aspergillus niger* | Biocatalysts Ltd. | 6'- |
| AY-30 | Candida sp. | Amano | 6'- |
| CCL-VII | *Candida cylindracea* | Sigma | 6'- |
| CEH-I | *Candida cylindracea* | E. Kodak | 6'- |
| CEH-II | *Candida cylindracea* | E. Kodak | A |
| CEH grade 2 | *Candida cylindracea* | E. Kodak | A |
| α-Chymotrypsin type II | *Bovine pancreas* | Sigma | B |
| CVL | *Chromobacterium viscosum* | Sigma | A |
| FAP-15 | Rhizopus sp. | Amano | A |
| GCI Lipase | Pseudomonas sp. | Genencor Int'l. | 6'- |
| α-Glucosidase (maltase) | Baker's yeast | Sigma | 1'- |
| β-Glucosidase | Almonds | Sigma | 6'-, 1'- |
| Invertase[1] grade V | Baker's yeast | Sigma | 6'- |
| L-700 (SAM-I) | *Pseudomonas fluoresens* | Mitsubishi | A |
| L-701 (SAM-II) | *Pseudomonas fluoresens* | Mitsubishi | A |
| L-703 (L-10) | *Candida lypolylica* | Amano | A |
| L-706 (CE-10) | *Humicola lanuginosa* | Amano | 6'- |
| L-707 (R-10) | *Penicillium roqueforti* | Amano | A |
| LP-160 (T-01) | *Chromobacterium viscostun* | Toyo Jozo | A |
| LP-119 | *Mucor miehei* | Novo | A |
| LP-302 (Lipase G) | Penicillim sp. | knano | A |
| Lipozyme | *Mucor miehei* | Novo | A |
| M-AP10 | Ymcor sp. | Amano | 6'- |
| *Mucor javanicus* | *Mucor javanicus* | Biocatalysts Ltd. | 6'- |
| *Mucor javanicus* | *Mucor javanicus* | Fluka | 6'- |
| *Mucor miehei* | *Micor miehei* | Biocatalysts Ltd. | A |
| N conc | *Rhizopus niveus* | Amano | A |
| P (Super Pec P) | *Aspergillus niger* | Amano | A |
| *Penicillium cyclopium* | *Penicillim cyclopium* | Biocatalysts Ltd. | 6'-, 1'- |
| PL-105 (Super Pec PL) | *Aspergillus niger* | Amano | 6'- |
| PLE | Pig liver esterase | Sigma | 1'- |
| PPL type VI-S | Porcine pancreas | Sigma | B |
| Proleather (protease) | *Bacillus subtilis* | Amano | B |
| Protease Type XIV | *Streptomyces griseus* | Sigma | 1'- |
| Proteinase K | *Aspergillus oryzae* | Int'l Biotech. | 6'- |
| *Rhizopus javanicus* | *Rhizopus javanicus* | Biocatalysts Ltd. | A |
| SAM-I | *Pseudomonas fluoresens* | Amano | A |
| Subtilopeptidase[2] | *Bacillus subtilis* | Boehringer Mannheim | B |
| Wheat germ | Wheat germ | Sigma | A |

A — Activity with no selectivity
B — No activity
[1]Invertase incubation was performed at 45° C., pH 4.5, 50 mM citrate-phosphate buffer
[2]Subtilisin incubation was performed at 45° C., pH 8.4, 20 mM potassium phosphate buffer enzymes or combinations thereof, which enzymes selectively hydrolyze individual components while enriching the amount of a desired ester. The enriched, non-hydrolyzed ester is then purified by standard methods.

As used herein an "appropriate solvent system" means an aqueous solution, preferably water or an organic solvent system comprising solvents such as tetrahydrofuran, dimethylsulfoxide, dimethylformamide, pyridine, acetone and similar solvents mixed in varying amounts with water.

Enzymes useful in the present invention are those enzymes which selectively hydrolyze specific components of the carbohydrate monoesters. Preferably these enzymes are regio-selective for the primary alcohols of the monoester mixtures. Useful enzymes include but are not limited to esterases, lipases, proteases and glycosidases. Specifically useful enzymes are those listed in Table 1, below, which enzymes were screened using the methods described in Example 1. When glycosidases are used, the reaction is not a selective hydrolysis of a specific primary alcohol, rather, the desired reaction is the selective hydrolysis of a disaccharide glycosidic bond.

The carbohydrate monoesters of the present invention may be any carbohydrate monoester. Without intending to be limited, the applicants have demonstrated the present invention with sucrose and/or glucose esters of varying fatty acids. Sucrose monoesters are perhaps the most important from a commercial standpoint and, therefore, are used as the primary examples in this invention. The carbohydrates include but are not limited to glucose, sucrose, lactose, cellobiose, raffinose, maltose, mannose, galactose and ribose. Such carbohydrates are monoesters of a fatty acid which comprises at least about 8 carbon atoms. Such fatty acids may comprise about 8 to about 22 carbon atoms and preferably are palmitate, caprate, laurate, myristate, stearate and oleate.

Experimental:

EXAMPLE 1

Enzyme Screening Methods

Three types of hydrolytic enzymes were screened: lipases (esterases), proteases and glycosidases. The general method is as follows:

General Procedure: Sucrose monopalmitate (Ryoto P-1760), 100 mg, was dissolved in 10 ml of 50 mM potassium phosphate buffer, pH 7.0, with heating. After cooling to room temperature (23° C.) 100 mg (dried powder) enzyme was added. Mixture was stirred at room temperature for up to five days. Samples (200 μL) were taken at 3 hours 1 day and, in some cases, five day intervals. After drying on hot plate under air stream the samples were derivatized with 1 ml of 1/1 mixture of pyridine and BSTFA (Pierce) with heating at 100° C. for 1 hour.

Analytical Method: Preliminary assignment of structures was determined by gc chromatography. Gc chromatograms showed that the three major peaks belonged to the three primary esters. This determination is made on the assumption that primary alcohols in esterification reactions, among others, predominate when there is a choice between primary and secondary alcohols. As a rule the primary alcohols react at least 10 times faster than the secondaries. Acid hydrolysis followed by analysis of products via gc showed that only glucose6-palmitate, for which a standard was available, results from treatment with acid. From the other two primary esters, only free glucose was observed.

Gas chromatographic analysis was performed on a DB-5 column, 15 m (J & W Scientific) with flame ionization detector, 1 μL injection. The starting temperature was 180° C. with a 10° per minute increase to 280° and a 6 minute holding time. Enzyme activity and specificity was estimated by comparing the areas under peaks corresponding to 6-O-, 1'-O- and 6'-O-esters.

Using the screening methods provided in this example, various classes of enzymes were tested. The screening summarized in Table 1 revealed five classes of enzymes: (1) those with no activity ("B"); (2) those with activity but no selectivity ("A"); (3) those with 6-O specificity; (4) those with 6'-O specificity; and (5) those with 1'-O specificity. In all cases, primary esters were attacked sit faster rates than secondary esters.

Based on the results of Example 1, three enzymes were selected for further study: *Candida cylindracea* lipase for 6-O position selectivity; *Mucor javanicus* lipase for 6'-O position selectivity; and *Penicillium cyclopium* lipase for 1'-O position selectivity. (In the case of *P. cyclopium* lipase, the 1'-O-ester was hydrolyzed much faster than the 6'-O-ester.)

EXAMPLE 2

CCL (Lipase) Hydrolysis of SMP

Sucrose monopalmitate (SMP) was used at a concentration of 10 mg/ml and *Candida cylindracea* lipase (CCL) (Sigma Type V) was added and dissolved at a concentration of 5 mg/ml. Incubation was performed with stirring at room temperature in water (no added buffers). Samples (200 μl) were taken at 5, 10, 20, 25, 30 and 60 minutes. The reaction was stopped by immersion in a dry ice-propanol bath. Samples were freeze dried for 2 hours and derivatized for gc analysis as described in Example 1. Areas under peaks were calculated and plotted. It was found that CCL has a pronounced selectivity for the 6-O-ester of sucrose.

EXAMPLE 3

Map-10 Digestion of SMP

Following the procedure substantially as set forth in Example 2, *Mucor javanicus* lipase (M-AP10) (10 mg/ml) was incubated with SMP. It was found that *Mucor javanicus* lipase (M-AP10) has a selectivity for the 6'-O-ester.

EXAMPLE 4

PC Digestion of SMP

Following the procedure substantially as set forth in Example 2, *Penicillium cyclopium* lipase (PC) (5 mg/ml) was incubated with SMP. It was found that *Penicillium cyclopium* lipase (PC) has a preference for the 1'-O-ester, followed by preference for the 6'-O-ester.

EXAMPLE 5

Assignment of GC Peaks

*Candida cylindracea* lipase (100 mg) was added to a sucrose monopalmitate mixture (100 mg) dissolved in 10 ml water. The mixture was stirred at room temperature for 1 hour and a 200 μl sample was taken for gc analysis. The mixture then was made up to 0.1N HCL and stirring was continued overnight at the same temperature. Samples were taken for gc analysis as described in Example 1.

A similar experiment was performed with *Mucor javanicus* lipase, except that the enzyme incubation time was 24 hours.

Review of the gc peaks revealed the following observations: Since only glucose-6-palmitate appeared in the hydrolysis sequence with Mucor lipase followed by acid hydrolysis, it was concluded that this enzyme had specificity for the 6'-O position and, by similar deduction, the Candida lipase had 6-O specificity. Therefore, the two largest gc peaks must belong to the primary esters at 6- and 6'- positions, while the next largest peak belongs to the 1'-ester, since it is well known that chemical esterification favors primary alcohols strongly over secondary alcohols.

EXAMPLE 6

Digestion of Sucrose Di- and Tri-Esters to SMP

To a water solution/suspension of a mixture of 500 mg of sucrose dipalmitates and tripalmitates one of the three enzymes (200 rag) detailed in Examples 2–5 is added. Samples are taken at 30 minute intervals and analyzed by previous methods. 6- specific enzymes give mostly monoesters of 6'-esters and 6'-specific enzymes give mostly monoesters of 6-esters.

EXAMPLE 7

Specific Hydrolysis of Glucose-6-palmitate

To a mixture of glucose palmitate monoesters (50 mg) dissolved in 10 ml, pH 7 potassium phosphate, 50 mM, was added 25 mg of *Candida cylindracea* lipase. Incubation was at 23° for one hour. Gc analysis revealed that the major ester hydrolyzed was the primary ester in the 6-position.

EXAMPLE 8

Enzymatic Conversion 6f Sucrose Di- and Tri-Palmitate Esters

Enzymatic conversion of sucrose di- and tri-palmitate esters (Ryoto P-370, 100 mg) dissolved in 10 ml of a 50% solution of tetrahydrofuran (THF) in water is incubated with 100 mg of *Candida cylindracea* lipase for two hours at 45° C. After lyophilization and successive extractions with hexane and THF, purified 6-O-sucrose palmitate is obtained. By substituting *Mucor javanicus* lipase for Candida lipase and extending incubation to 20 hours, a purified sample of 6'-O-sucrose palmitate is obtained. Further, if it is desired to remove the 1'-ester from these preparations, a 20 minute incubation with *Penicillium cyclopium* lipase (10 mg/ml) is carried out.

What is claimed is:

1. A regio-selective biosynthetic process for the resolution of a 1'-O-, 6'-O- or 6-O- ester from a mixture of carbohydrate monoesters, the process comprising:
   a) obtaining a mixture of carbohydrate monoesters;
   b) incubating the mixture with one or more regio-selective lipase in the presence of a water solvent system to provide selective hydrolysis of the 1'-O-, 6'-O- or 6-O- ester; and
   c) isolating the 1'-O-, 6'-O- or 6-O- ester of interest.

2. A process of claim 1 wherein the mixture of carbohydrate monoesters is a mixture of regio-isomers of carbohydrate monoesters of a fatty acid of at least about 8 carbons.

3. A process of claim 2 wherein the carbohydrate is sucrose or glucose.

4. A process of claim 2 wherein the fatty acid is about 8 carbons to about 22 carbons.

5. A process of claim 1 wherein the fatty acid is palmitate and the carbohydrate is sucrose.

6. A process of claim 1 wherein the regio-selectivity of the enzyme is at a primary alcohol in the carbohydrate.

7. A process of claim 1 wherein the solvent system further comprises a buffer.

8. A process of claim 1 wherein the lipase reacts selectively at the 6 position in such mixture of carbohydrate monoesters.

9. A process of claim 8 wherein the lipase is derived from *Candida cylindracea*.

10. A process of claim 1 wherein the lipase reacts selectively at the 6' position in such mixture of carbohydrate monoesters.

11. A process of claim 10 wherein the lipase is derived from a *Mucor javanicus*.

12. A process of claim 1 wherein the lipase reacts selectively at the 1' position in such mixture of carbohydrate monoesters.

13. A process of claim 12 wherein the lipase is derived from *Penicillium cyclopium*.

* * * * *